(12) United States Patent
Dougherty et al.

(10) Patent No.: US 9,999,779 B2
(45) Date of Patent: Jun. 19, 2018

(54) CELL, TISSUE AND ORGAN PROTECTION USING A MAGNETIC FIELD

(71) Applicant: The Trustees of The University of Pennsylvania, Philadelphia, PA (US)

(72) Inventors: Lawrence Dougherty, Wenonah, NJ (US); James J. Pilla, Kennett Square, PA (US); Keith A. Cengel, Bala Cynwyd, PA (US); Alireza Kassaee, Glenmoore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 134 days.

(21) Appl. No.: 15/032,645

(22) PCT Filed: Oct. 29, 2014

(86) PCT No.: PCT/US2014/062837
§ 371 (c)(1),
(2) Date: Apr. 28, 2016

(87) PCT Pub. No.: WO2015/066137
PCT Pub. Date: May 7, 2015

(65) Prior Publication Data
US 2016/0263390 A1    Sep. 15, 2016

Related U.S. Application Data

(60) Provisional application No. 61/896,932, filed on Oct. 29, 2013.

(51) Int. Cl.
*A61N 5/02* (2006.01)
*A61N 2/00* (2006.01)
(Continued)

(52) U.S. Cl.
CPC ............... *A61N 2/002* (2013.01); *A61N 1/16* (2013.01); *A61N 2/02* (2013.01); *A61N 2/06* (2013.01);
(Continued)

(58) Field of Classification Search
CPC . A61N 1/16; A61N 2/00; A61N 2/004; A61N 2/02; A61N 2/06; A61N 5/00
(Continued)

(56) References Cited

U.S. PATENT DOCUMENTS 5,968,527 A    10/1999  Litovitz
6,926,659 B1    8/2005  Sandstrom
2007/0184057 A1    8/2007  Litovitz et al.

OTHER PUBLICATIONS

Alikamanoglu et al., "Effect of Magnetic field and Gamma radiation on Paulownia Tomentosa Tissue Culture", Plant Cell Tissue and Organ Culture, Oct. 2005, 83(1), 109-114.
(Continued)

*Primary Examiner* — John Lacyk
(74) *Attorney, Agent, or Firm* — Baker & Hostetler LLP

(57) ABSTRACT

Methods and apparatus are provided for applying low magnetic fields (<400 G) to mammalian cells, tissues and organs for protection from the damaging effects of ionizing radiation and other oxygen dependent injuries that involve the radical pair mechanism. The magnetic fields are generated by fixed magnets or active magnets and used to enhance the survival of healthy cells during radiation treatment for cancer, to protect workers from radiation within nuclear power plants, to protect astronauts from radiation during long space voyages, to increase working time in exposed environments, to provide a safe room in hazardous locations, and to protect normal tissue during radiation treatment and in medical imaging modalities that use ionizing radiation (X-ray, CT, mammography). The method described herein may also be used to mitigate the damaging effects of
(Continued)

reperfusion, stroke, oxygen toxicity, inflammation, autoimmune disease, and the like by applying protective magnetic fields.

14 Claims, 7 Drawing Sheets

(51) Int. Cl.
    *A61N 2/02*     (2006.01)
    *A61N 2/06*     (2006.01)
    *A61N 1/16*     (2006.01)
    *A61N 5/10*     (2006.01)

(52) U.S. Cl.
    CPC ........ *A61N 5/10* (2013.01); *A61N 2005/1094* (2013.01)

(58) Field of Classification Search
    USPC ...................................................... 600/1–15
    See application file for complete search history.

(56) References Cited

OTHER PUBLICATIONS

Asano et al., "Pathogenesis and protection of ischemia and reperfusion injury in myocardium", Journal of Nippon Medical School, 2003, 70, 384-392.
Buchacenko, "Magnetic Isotope Effect: Nuclear Spin Control of Chemical Reactions", The Journal of Physical Chemistry A, Nov. 2001, 105, 44, 9995-10011.
Buchacenko, "MIE versus CIE: Comparative Analysis of Magnetic and Classical Isotope Effects", Chemical Reviews, Nov. 1995, 95, 2507-2528.
Grissom, "Magnetic Field Effects in Biology: A Survey of Possible Mechanisms with Emphasis on Radical-Pair Recombination", Chemical Reviews, 1995, 95(1), 3-24.
Pietrofesa et al., "Radiation mitigating properties of the lignin component in flaxseed", BMC Cancer, 2013, 13, 179, 18 pages.
Rockwell, "Influence of a 1400-gauss Magnetic Field on the Radiosensitivity and Recovery of EMT6 Cells in Vitro", Int. J. Radiat. Biol., 1977, vol. 31, No. 2, 153-160.
Sarvestani et al., "Static Magnetic Fields Inhibit Radiation-Induced Apoptosis in Bone Marrow Stem Cells", Proceeding of The 5th International Workshop on Biological Effects of Electromagnetic, 2008, 7 pages.

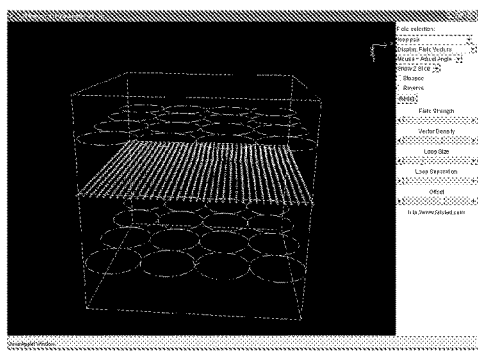
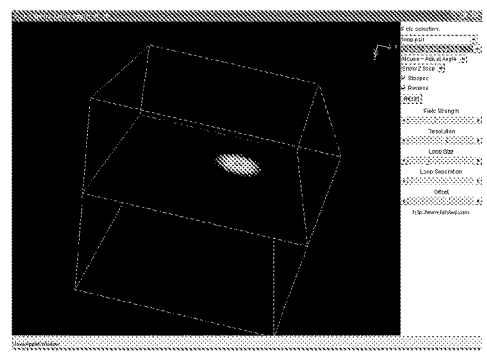
FIG. 6A
FIG. 6B

CELL, TISSUE AND ORGAN PROTECTION USING A MAGNETIC FIELD

CROSS REFERENCE TO RELATED APPLICATION

This application is a National Stage Application filed under 35 U.S.C. 371 of International Application No. PCT/US2014/062837 filed Oct. 29, 2014, which claims priority to U.S. Provisional Application No. 61/896,932, filed Oct. 29, 2013. The contents of that patent application are hereby incorporated by reference herein.

TECHNICAL FIELD

The invention relates to methods and apparatus for protecting human cells, tissues and organs from the damaging effects of ionizing radiation during radiation treatment and in medical imaging modalities that use ionizing radiation (e.g., X-rays and CT), and the damaging effects of diseases and injuries of the body involving the radical pair (RP) mechanism, such as reperfusion, stroke, oxygen toxicity, inflammation, autoimmune disease, and the like, by applying a protective magnetic field that reduces the reactivity of the radicals and thereby the damaging effect on the cells.

BACKGROUND

The mechanism of magnetic field radioprotection is based on the principle of nuclear and electron spin conservation. Spin is an intrinsic quantum mechanical property of the electron and can be characterized as being either "up" or "down". All chemical reactions are spin selective and allow only for those spin states of reactants in which the total spin is identical to that of products. Therefore, if one can control the spin states, one can control the chemical reaction. This is important since it allows for a magnetic interaction that can be used as a mechanism for control of that reaction. Control is achieved using an external magnetic field produced by either permanent magnets or electromagnetic coils. The magnetic field causes spin conversion that switches the reaction from a spin forbidden to a spin-allowed state. Not all reactions can be controlled in this manner but those that show this magnetic field effect (MFE) (e.g., Buchachenko A L, *MIE versus CIE: Comparative Analysis of Magnetic and Classical Isotope Effects*, Chem. Rev. 95, 2507-2528 (1995), and Buchachenko A L, *Magnetic Isotope Effect: Nuclear Spin Control of Chemical Reactions*, Phys. Chem. 105, 44, (2001)) have spin-selective processes, such as the radical pair mechanism (RPM). For radical pairs (RP), the magnetic field increases the probability of allowed spin states and thus an enhancement of radical pair recombination. (See, e.g., Grissom, C. B., *Magnetic Field Effects in Biology: A Survey of Possible Mechanisms with Emphasis on Radical-Pair Recombination*, Chem. Rev., 95(1), 3-24 (1995).)

In radiotherapy, radiolysis of water molecules produces highly reactive radicals—including hydrogen radical (H.), and a hydroxyl radical (OH.). An additional radical is formed when the hydrogen radical interacts with molecular oxygen to form highly reactive hydroperoxyl radical ($HO_2$'). The inventors propose that the magnetic field effect will reduce the damaging effects of the radicals and the subsequent cell damage. There is little rigorous research on this topic and some of the literature seems contradictory on whether a low static magnetic field is positive, negative or has no biological effect. What is clear is that no researcher has done a systematic study of the biological effect of low static fields during radiolysis. For example, Rockwell reported in an article entitled *Influence of a 1400-gauss Magnetic Field on the Radiosensitivity and Recovery of EMT6 Cells* in Vitro, Department of Therapeutic Radiology, Yale University, School of Medicine, 333 Cedar Street, New Haven, Conn., 06510, U.S.A, 1977, Vol. 31, No. 2, Pages 153-160, that there was no effect on radiosensitivity using a low static magnetic field during radiation exposure. However, only a single field strength of 1400 G was used. The present inventors' research shows that that such a field would have been too large to see an effect. In supporting literature, Sarvestani, et al. reported in an article entitled *Static Magnetic Fields Inhibit Radiation-induced in Bone Marrow Stem Cells*, Department of Biophysics, Faculty of Bioscience, Tarbiat Modares University, Tehran, Iran, a 20% improvement in survival of bone marrow stem cells when exposed to 0.5 Gy radiation and 5-30 G magnetic field. Alikamanoğlu et al. reported in an article entitled *Effect of Magnetic field and Gamma radiation on Paulowinia Tomentosa Tissue Culture*, Plant Cell Tissue and Organ Culture, 83(1): 109-114, on the regenerative effects of a low magnetic field to plant cells when exposed to 10-25 Gy gamma radiation. Also, U.S. Pat. No. 6,926,659 describes the combination of applying a magnetic field during irradiation but claims that the combination of the two methods enhances cell death, which is precisely the opposite of the results obtained by the inventors and described below.

Thus, the prior art provides contradictory evidence regarding whether there is an effect when a magnetic field is applied to irradiated cells.

SUMMARY

In sharp contrast with the prior art, the present inventors have discovered a relatively simple, non-toxic mechanism of protecting human cells from the damaging effects of ionizing radiation during radiation treatment and in medical imaging modalities such as X-ray, CT, mammography, etc., and the damaging effects of diseases and injuries of the body involving the radical pair mechanism, such as reperfusion, stroke, oxygen toxicity, inflammation, autoimmune disease, and the like using a low intensity static magnetic field. In addition, the methods described herein may be used to increase working time in exposed environments, provide a safe room in hazardous locations, and allow extended space flight for astronauts.

The majority of the damage from ionizing radiation, including cardiac reperfusion, stroke, oxygen toxicity, inflammation, autoimmune disease, and the like, is caused by the reactive free radicals produced from water that attack the biomolecules within the cells, causing damage or death. The methods described herein provide a method of cell protection that is achieved using a magnetic field in the range of 20-400 G when applied to the patient, that reduces the effects of the damaging free radicals generated by the ionizing radiation during reperfusion, stroke, oxygen toxicity, inflammation, autoimmune disease, and the like. The inventors show that in the presence of an external magnetic field, the damaging effects of the radicals are reduced and thereby diminish cell damaging effects. In experiments that exposed cells to low magnetic fields during exposure to ionizing radiation, the inventors showed a dramatic impact on clonogenic survival, increasing the surviving fraction by up to 50%. In another experiment where cells were exposed to 24 hour hypoxia followed by 2 hours of reperfusion with and without a magnetic field, the cells protected with the magnetic field expressed significantly decreased DNA damage compared to reperfusion without the magnetic field.

In exemplary embodiments, a method of reducing the effective dose of ionizing radiation in a patient and/or reducing the damaging effects of cardiac reperfusion, stroke, oxygen toxicity, inflammation, autoimmune disease, and the like includes applying a magnetic field having a field strength of between 20 G and 400 G, preferably 60 G to 300 G, to normal cells or cardiomyocytes of a patient diagnosed or believed to have experienced injury from cardiac ischemic reperfusion, oxygen toxicity, chronic inflammation, autoimmune diseases, or stroke. The corresponding apparatus includes a source of magnetic field from a permanent magnet or active electro-magnet to be applied simultaneously with the radiation dose or during the time of injury from cardiac reperfusion, stroke, oxygen toxicity, inflammation, autoimmune disease, and the like.

BRIEF DESCRIPTION OF THE DRAWINGS

The various novel aspects of the invention will be apparent from the following detailed description of the invention taken in conjunction with the accompanying drawings, of which:

FIG. 6 illustrates a simulation of a multi-element magnetic field coil design in which a null region can be created in one region while preserving the field outside of that area by varying the current in each element. Layout of the coils and the vector field is shown in FIG. 6A with the magnitude of the vector field shown in FIG. 6B.

DETAILED DESCRIPTION OF ILLUSTRATIVE EMBODIMENTS

The invention will be described in detail below with reference to FIGS. 1-7. Those skilled in the art will appreciate that the description given herein with respect to those figures is for exemplary purposes only and is not intended in any way to limit the scope of the invention. All questions regarding the scope of the invention may be resolved by referring to the appended claims.

Data

To test whether magnetic fields (MF) could modify cellular radiosensitivity, the inventors developed a customized apparatus using fixed field magnets (e.g., permanent magnets or active electro-magnets) (FIG. 1A) and exposed SQ20b head and neck cancer cells to magnetic fields ranging from 0-1000 G during irradiation with 2 Gy MV photons and determined clonogenic survival. This cell line and dose were chosen since the inventors have extensive previous experience demonstrating that the survival of these cells following 2 Gy exposure leads to 60-70% of cells surviving. In addition, this is a cell line for which typical DMF (dose modifying factor, which quantifies the impact of an agent on the dose of radiation needed to achieve a given effect) for most radiation modifying agents rarely exceeds a 20% change from baseline (corresponding to DMF values of 0.8 or 1.2). As illustrated in FIG. 1B, these experiments reveal that magnetic fields in the range of 20-400 G, preferably 60-300 G, can have a profound radioprotective effect on cells, increasing survival of mammalian cells following exposure to ionizing radiation by more than 1.6 fold to levels comparable to unirradiated controls.

As illustrated in FIG. 1B, the peak radioprotective effect is seen at field strengths below 400 G. Fields of this strength are easily achieved using electro-magnets for large scale use or the placement of permanent magnets for smaller applications. Clinical applications in radiotherapy may be achieved using a coil-pair that permits creation of a null magnetic field region in the same target region of radiation exposure while maintaining the field outside this area, thus providing protection.

Figure 1:
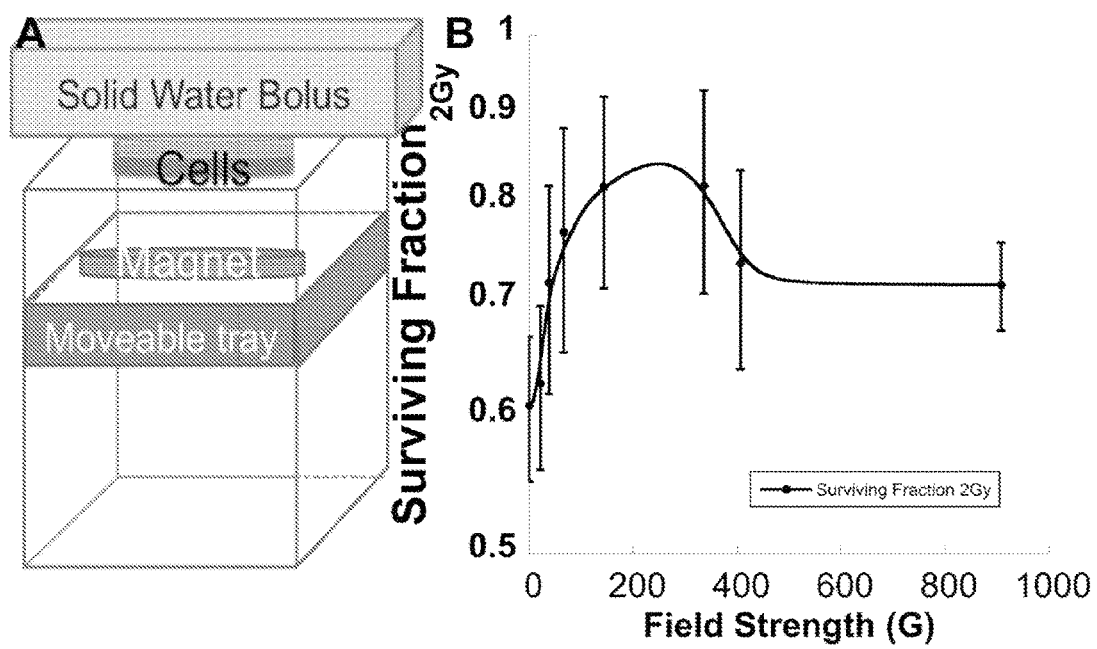
FIG. 1 illustrates A) a permanent magnet device and B) the effects of magnetic fields on radiation survival.

This experiment was repeated on two subsequent dates yielding an average improvement in cell survival of cancer cells by 50%. Note that this effect was independent of X-ray source (kV or mV) or MF source. MF had no impact on physical radiation dose delivered using either device (permanent magnet or electromagnetic coils). In FIG. 1, data are mean±sd for a 2 MV, 1 kV x-ray experiment.

Figure 2:
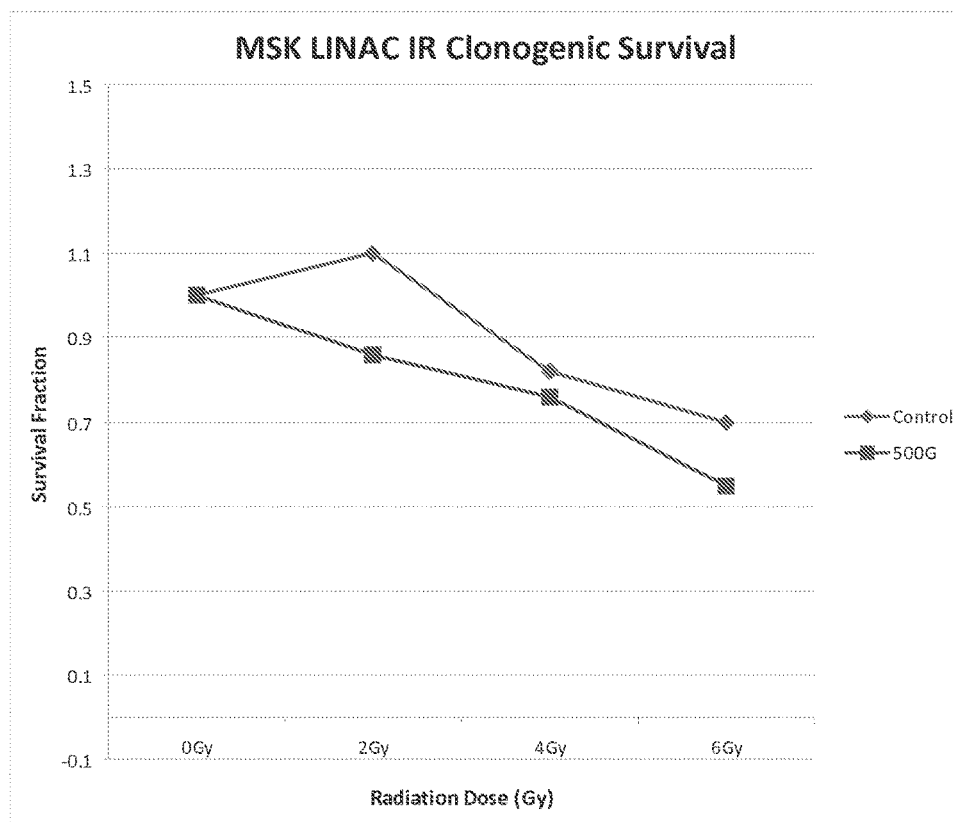
FIG. 2 illustrates clonogenic survival fraction as a function of radiation dose with cells exposed to a 500 G magnetic field, showing that there is no protective effect seen at this field strength.
Figure 3:
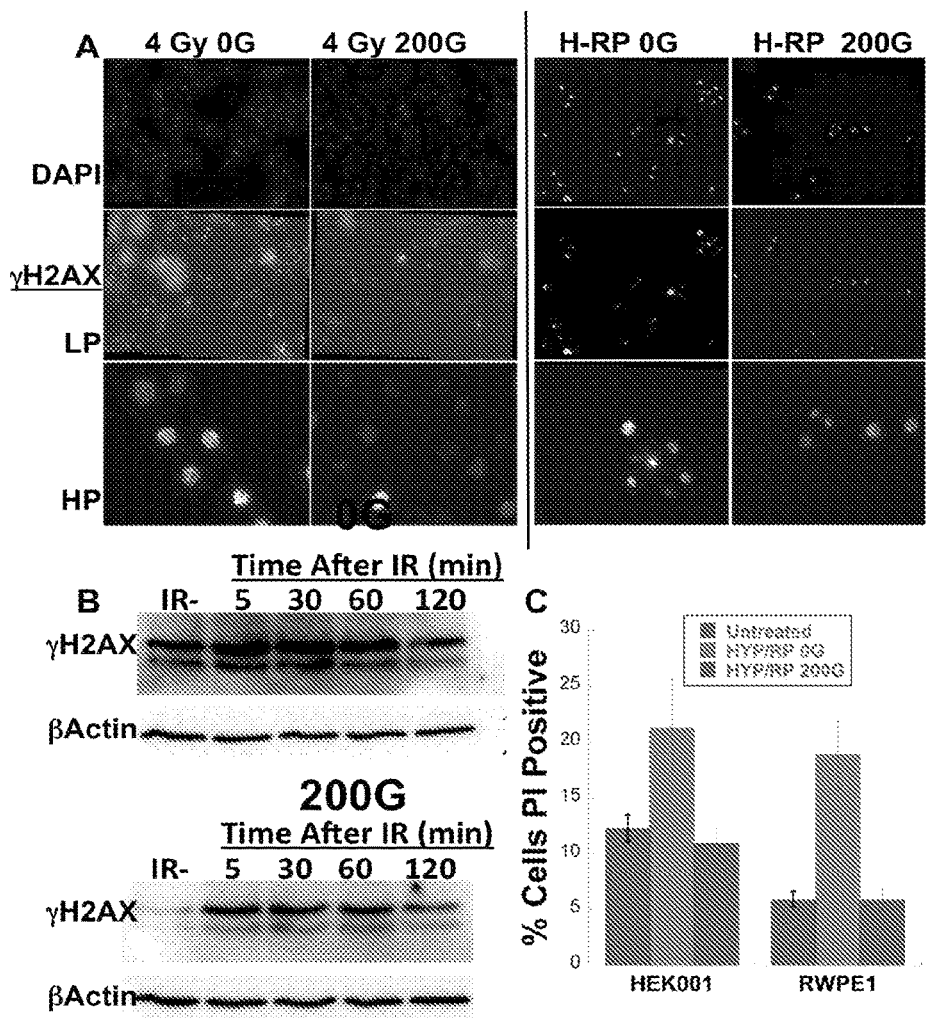
FIG. 3 illustrates A) γH2Ax staining of HEK001 cells after 2 Gy IR (left panel) or hypoxia-reperfusion (right panel) with or without 200 G MF, B) western blot analysis of IR± MF, and C) PI analysis of membrane damage.

By comparison, FIG. 2 illustrates clonogenic survival fraction as a function of radiation dose with cells exposed to a 500 G magnetic field. As illustrated, there is no protective effect seen at this field strength, showing the selectivity of the applied field strength for clonogenic survival.

Initial mechanistic studies were performed using immunocytochemical staining for γH2Ax to detect DNA double strand breaks (DSB) in HEK001 (normal squamous) cells after treatment with 2 Gy of x-rays with or without a 200 G MF during irradiation using techniques described in the art (e.g., Pietrofesa, et al., *Radiation mitigating properties of the lignan component in flaxseed*, BMC Cancer, 2013, 13: 179, PMC:3636021). Decreased γH2Ax foci were observed at 30 min, strongly suggesting that the MFE involves protection from the initial DNA damage event rather than increased repair. FIG. 3A illustrates γH2Ax staining of HEK001 cells after 2 Gy IR (left panel) with or without 200 G MF, while FIG. 3B illustrates western blot analysis of IR±MF, and C) PI analysis of membrane damage.

To determine whether the MFE specifically targeted free radicals, HEK001 or RWPE1 (normal prostate) cells were placed in hypoxia for 2 hours and re-perfused for 4 hours with atmospheric $O_2$ in a tissue culture incubator with or without a 200 G magnetic field. This process generates widespread damage to cellular macromolecules, including membranes and DNA, that is almost entirely dependent on hydroxyl radicals generated from peroxide and divalent cations (e.g. Fe2+) through the Fenton reaction described by Asano, et al. in an article entitled *Pathogenesis and protection of ischemia and reperfusion injury in myocardium*, J Nippon Med Sch, 2003, 70: 384-92. FIG. 3A further illustrates γH2Ax staining of HEK001 cells after 2 Gy hypoxia-reperfusion (right panel) with or without 200 G MF. Membrane damage was determined by the ability to exclude the dye propidium iodide (PI) and DNA damage was assessed by γH2Ax staining as shown in FIG. 3C. These experiments demonstrate that the MFE extends to protecting both DNA and membrane damage from hypoxia-reperfusion induced hydroxyl radical mechanism.

Taken together, these data suggest that MFE can protect cells from radiation-induced, hydroxyl radical-mediated DNA DSB and that the underlying mechanism is generalizable to protecting multiple cellular macromolecules from hydroxyl mediated damage, regardless of the source of the radicals. In particular, the inventors have observed that if a low magnetic field (e.g., 60-300 G) is applied simultaneously with 2 Gy radiation exposures that the survival of cancer cells is increased by 30-50%. The experiment was repeated, for a total of three experiments, on plates of cancer cells using three different radiation sources with similar results obtained. By protecting cells from radiation-induced DNA damage, the MFE has the potential to not only protect cells from the cytotoxic effects of ionizing radiation, but also to reduce the rate of mutations in surviving cells, thereby dramatically decreasing the rate of radiation-induced malignancies. Since many diseases and injuries of the body involve the radical pair mechanism (e.g., cardiac ischemic reperfusion, stroke, oxygen toxicity, chronic inflammation, autoimmune diseases, and the like), a protective effect can be expected in these applications as well.

Figure 4:
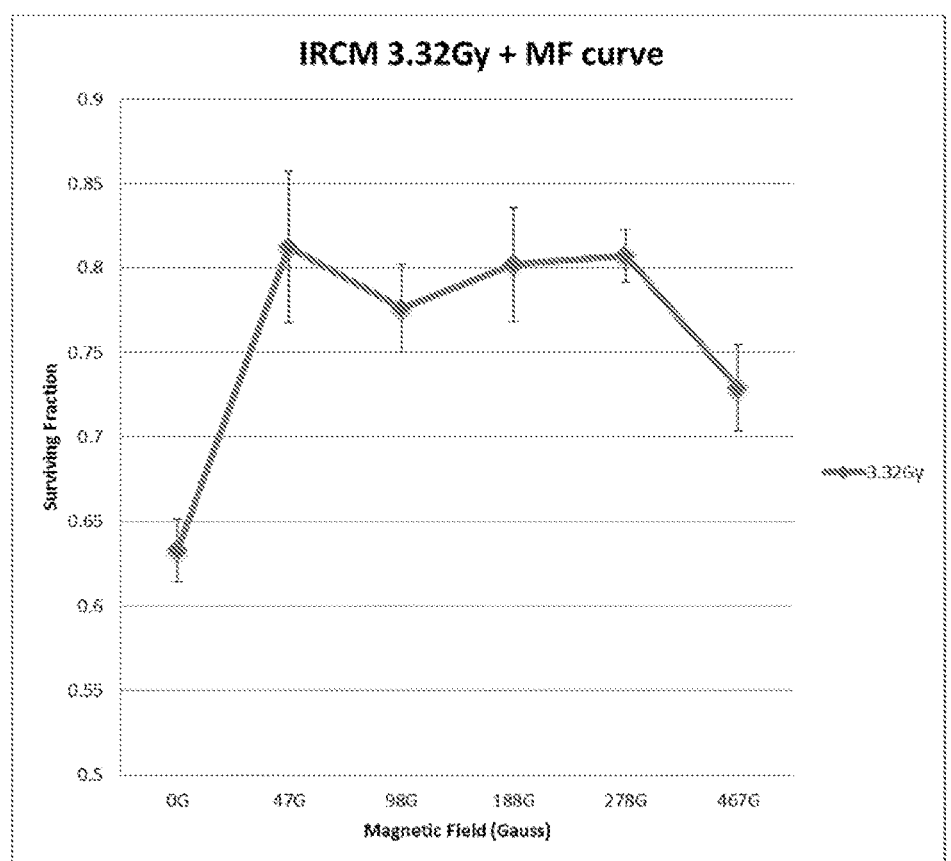
FIG. 4 illustrates that cell survival increased up to 30% when using a static field between 47 and 278 Gauss on cardiomyocytes.

A further protective effect from radiation induced damage using a magnetic field has been demonstrated with rat cardiomyocytes. This is an important cell line since incidental irradiation of the heart during radiation treatment of the lung or breasts is a significant side effect of radiation therapy Immortalized rat cardiomyocytes (IRCM) in culture were irradiated with a dose of 3.3 Gy in the presence of a magnetic field that ranged from zero to 400 Gauss. As shown in FIG. 4, cell survival increased up to 30% when using a static field between 47 and 278 Gauss.

Another area of MFE protection is cardiac myocytes during reperfusion following an infarct or other cardiac event which decreases oxygen to the cells (ischemia/reperfusion I/R). Cardiac I/R injury occurs when oxygenated blood is returned to the myocytes subsequent to a period of no blood flow. A major source of I/R injury is the production of free radicals from oxygen which generates reactive oxygen species (ROS). ROS are produced within minutes of reperfusion and continue to be generated for hours after the restoration of blood flow to ischemic myocardium. Free radicals damage myocytes directly by effecting membrane proteins and phospholipids which leads to fatal metabolic and structural derangements. In addition, free radicals can directly damage DNA and RNA resulting in altered cell function and death. Decreasing the generation of free radicals following reperfusion would have a profound effect on cell survival and outcome.

Figure 5:
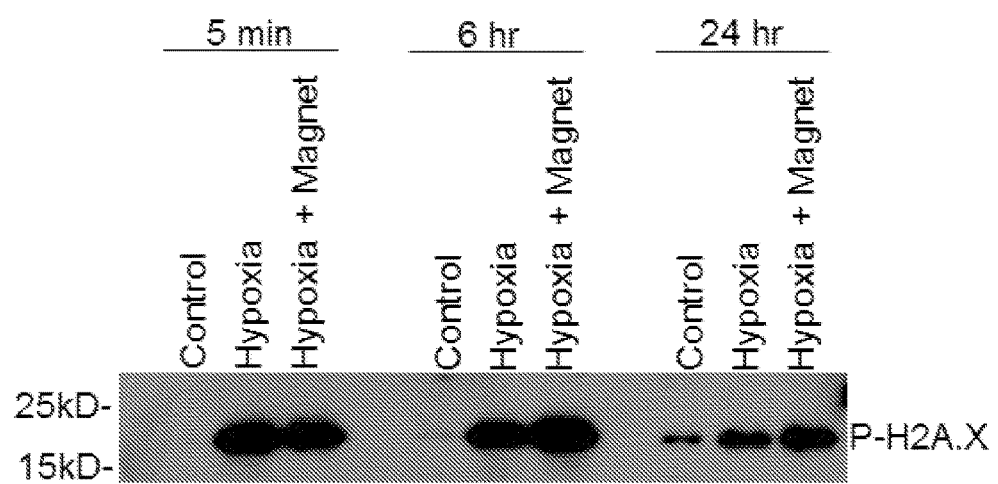
FIG. 5 illustrates the beneficial effect of the magnetic field (MFE) on immortalized rat cardiomyocytes (IRCM) exposed to 24 hour hypoxia followed by 2 hours of reperfusion (atmospheric $O_2$) with and without MFE. As illustrated, immediately following the 2 hours of reperfusion, the cells protected with the magnetic field expressed significantly decreased DNA damage compared to reperfusion without the magnetic field.

Magnetic field effect (MFE) can protect myocytes from I/R damage by promoting the recombination of radical pairs decreasing free radical formation and cellular damage. I/R experiments performed using rat cardiomyocytes (RCM) demonstrated the beneficial effect of MFE. In the acute MFE experiment, RCM were exposed to 24 hour hypoxia followed by 5 minutes of reperfusion (atmospheric $O_2$) with and without MFE. As shown in FIG. 5, immediately following the 5 minutes of reperfusion, the MFE cells expressed significantly less phosph-H2A.X (decreased DNA damage) compared to reperfusion without the magnetic field. DNA damage increased at 6 hours when the magnetic field was removed signifying that withdrawing the field eliminates the protective effect during reperfusion.

Subsequent experiments with the magnetic field applied chronically demonstrated sustained MFE protection. Continuous MFE protection for 6 hours decreased expression of phosph-H2A.X in the cells as measured by western blot, demonstrating reduced DNA damage.]. The level of MFE protection increased at 6 hours compared to the acute time point (5 minutes post reperfusion).

Discussion

Those skilled in the art will appreciated that the applications of this discovery are significant, particularly for the protection of normal tissue during radiation treatment and in imaging modalities that use ionizing radiation. In addition there are commercial, industrial and military applications that are far reaching.

In the field of radiation oncology, even using the most sophisticated treatment planning, normal tissue near the treatment area receives a significant dose of radiation. This not only increases the risk of cancer but also has an effect on the quality of life. For application of MFE to radiation therapy, a zero field (null field) is desired in the area of treatment to allow the intended radiation dose to the cancer cells. However, the normal tissue and organs around the treatment are would need the protective magnetic field. Using a multi-element coil design as illustrated in FIG. 6, a null could be created of various shapes and dimension by adjusting the electrical current in each of the coil elements. In particular, FIG. 6 illustrates a simulation of a multi-element magnetic field coil design. By varying the current in each element, a spherical null region can be created in one region (FIG. 6A) while preserving the field outside of that area. This simulates the treatment plan for a malignant focal mass. Layout of the coils and the vector field is shown in FIG. 6A. The magnitude of the vector field is shown in FIG. 6B. The bright region corresponds to the null field created by the coil. The area outside the null region would be protected by the MFE while the tissue within the prescribed volume would be treated normally.

Figure 7A:
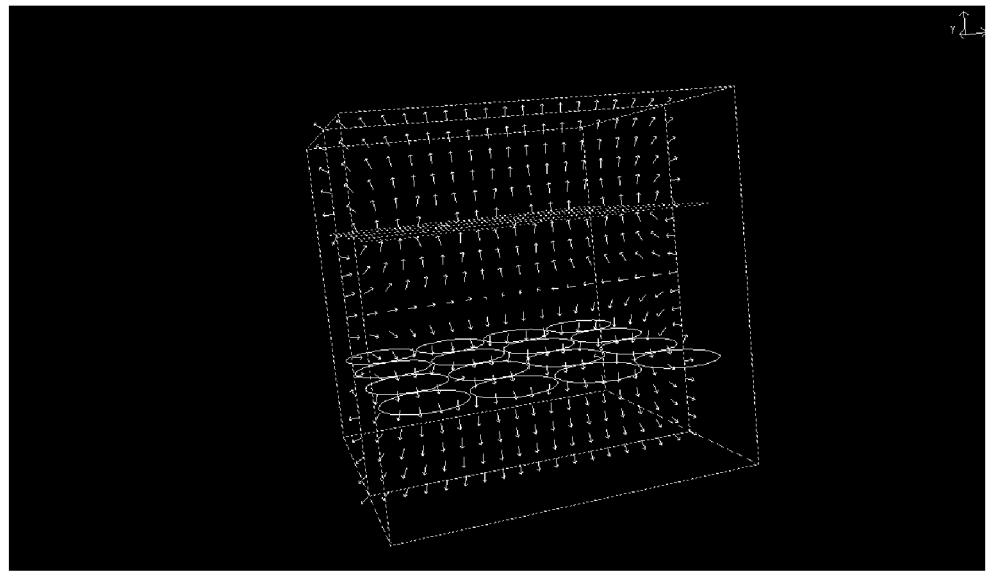
FIG. 7 illustrates an additional magnetic field simulation with the currents in the coil elements adjusted to create a null field in a cylindrical volume to simulate a radiation treatment plan for the spine that protects tissues and organs outside of the treatment volume while allowing the radiation dose to the cancer cells within the volume. The vector field is shown in FIG. 7A with the magnitude of the vector field shown in FIG. 7B.
Figure 7B:
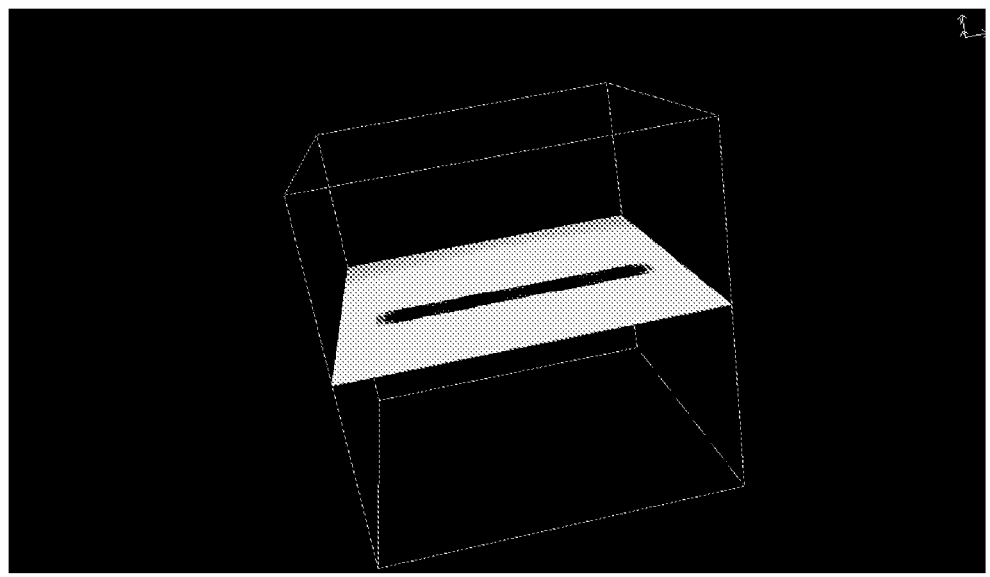

FIG. 7A shows an additional magnetic field simulation with the currents in the coil elements adjusted so as to create a null field in a cylindrical volume. As shown in FIG. 7B, this simulates a radiation treatment plan for the spine that protects tissues and organs outside of the treatment volume while allowing the radiation dose to the cancers cells within the volume. Design, fabrication and integration of these tools into the treatment planning software would be an important part of radiation oncology. A 32-channel coil design suitable as a torso coil is shown in FIGS. 6 and 7, but coil arrays using different number or sized elements or at different orientations is a logical extension of the invention.

Additionally, there is rising concern over the cumulative radiation dose from diagnostic X-rays and CT scans. This is compounded by the increase use in screening large portions of the population (breast mammography, lung CT). In this application, the creation of the magnetic field is easier than in the oncology application—a simple pair of current loops or permanent magnets would create a field that would reduce the effective dose from the ionizing radiation. For example, in mammography, a pair of rectangular coils may be built into the compression plates to create a protective homogeneous field through the entire breast.

In industrial and military applications, personnel in hazardous areas could be protected in safe rooms—rooms in which magnetic field coils have been built into the walls to create a low static field that reduces the effective dose of the radiation. The magnetic field discussed herein is very small and easily created with simple coil loops. It is even feasible that, with further coil development, a protective suit with embedded coils creating a low magnetic field directed inward may be manufactured for personnel moving around in hazardous radiation environments. The method described herein has the potential to provide a radioprotector that could be stockpiled with an indefinite shelf life and could be used to treat larger populations inexpensively and safely.

As mentioned above, cellular protection via the magnetic field effect can be used in other disease and injury applications. For example, cell damage during hypoxia and reperfusion is caused not only by the decrease in energy supply but also by oxidative stress. Hypoxic injury is exacerbated by reperfusion and is an important mechanism of cellular injury and a major clinical problem in treating ischemia in organs such as the heart and brain. It is widely recognized that free radical formation plays a major role in cell damage during reperfusion. Free radicals are produced within minutes of reperfusion and continue to be generated for hours after the restoration of blood flow to ischemic tissue. Several mechanisms have been proposed for the development of these free radicals including xanthine oxidase, activated neutrophils, electron leakage from ischemic mitochondrion, catecholamine oxidation, as well as cyclooxygenase and lipoxygenase enzymes. Free radicals damage cells directly by altering membrane proteins and phospholipids. Because these membrane constituents play crucial roles as receptors, enzymes, and ion channels, free radical injury can lead to fatal metabolic and structural derangements. Reperfusion produced free radicals cause significant oxidative damage to DNA which, if not repaired, results in cell death.

Existing therapies for reperfusion injury linked to free radicals include the use of antioxidants and tissue cooling. Antioxidants are believed to decrease reperfusion injury by inhibiting free radical formation and the scavenging of free radicals produced. Despite positive observations in classic models of experimental ischemia and reperfusion, clinical experience with antioxidants has been disappointing. Tissue cooling works under the premise that metabolism will be decreased at lower temperatures thus diminishing free radical formation. Preliminary pre-clinical results have shown a decrease in free radical formation and apoptosis with tissue cooling.

Treatment to diminish reperfusion injury using the methods of the invention uses the magnet field effect (MFE) to reduce the damaging effects of the radicals that cause cellular damage. MFE alters the state of the free radicals reducing their reactivity prior to becoming mobile and interacting with cellular components resulting in damage. DNA repair may also be directly affected by MFE decreasing the resulting cell death. Those skilled in the art will appreciate that the methods of the invention may be used as a therapy to reduce reperfusion injury in organs such as the heart and brain. MFE at optimal strength, duration and oscillation applied during reperfusion will result in improved cell survival and organ function.

Those skilled in the art will also appreciate that the invention may be applied to other applications and may be modified without departing from the scope of the invention. Further optimization may yield even more impressive results. Moreover, as noted above, the protective effects of the invention as expected for other diseases and injuries of the body that involve the radical pair mechanism (e.g., cardiac ischemic reperfusion, stroke, oxygen toxicity, chronic inflammation, autoimmune diseases, and the like. Accordingly, the scope of the invention is not intended to be limited to the exemplary embodiments described above, but only by the appended claims.

What is claimed:

1. A method of treating diseases and injuries of a patient's body involving a radical pair mechanism, comprising:
    exposing a patient to a source of ionizing radiation; and
    simultaneously applying to the patient a first magnetic field having a field strength of between 20 G and 400 G.

2. A method as in claim 1, wherein the first magnetic field is applied to a patient diagnosed or believed to have experienced injury from cardiac ischemic reperfusion, oxygen toxicity, chronic inflammation, autoimmune diseases, or stroke.

3. A method as in claim 1, wherein the first magnetic field strength is between 20 G and 400 G and is applied to normal cells of the patient.

4. A method as in claim 3, wherein the first magnetic field strength is between 60 G and 300 G.

5. A method as in claim 2, wherein the first magnetic field strength is between 20 G and 400 G and is applied to cardiomyocytes of the patient.

6. A method as in claim 5, wherein the first magnetic field strength is between 60 G and 300 G.

7. An apparatus for effectively reducing the effective dose of ionizing radiation applied to a patient, comprising:
    a source of ionizing radiation to which the patient is exposed; and
    a permanent magnet or active electro-magnet that generates a first magnetic field having a field strength of between 20 G and 400 G that applies said first magnetic field to the patient while the patient is exposed to said ionizing radiation.

8. An apparatus as in claim 7, wherein the first magnetic field strength is between 60 G and 300 G.

9. A method of reducing the effective dose of ionizing radiation in a patient exposed to the ionizing radiation and/or reducing the damaging effects of a patient experiencing cardiac reperfusion, stroke, oxygen toxicity, inflammation, or autoimmune disease, comprising:
    applying a magnetic field having a field strength of between 20 G and 400 G to normal cells or cardiomyocytes of a patient diagnosed or believed to have experienced injury from cardiac ischemic reperfusion, oxygen toxicity, chronic inflammation, autoimmune diseases, or stroke.

10. A method as in claim 9, wherein the field strength is between 60 G and 300 G.

11. The method of claim 1, wherein the first magnetic field is characterized as static.

12. The method of claim 1, wherein the first magnetic field is applied to a first region of the patient and further comprising applying to a second region of the patient a second magnetic field having a field strength of less than 20 G.

13. The apparatus of claim 7, wherein the apparatus is configured to apply the first magnetic field to a first region of the patient while applying a second magnetic field of less than 20 G to a second region of the patient.

14. The apparatus of claim 7, wherein the first magnetic field is characterized as static.

* * * * *